United States Patent [19]

Paz

[11] 4,277,343
[45] Jul. 7, 1981

[54] METHOD FOR CONTINUOUSLY MONITORING AND CONTROLLING ALKALINITY FOR ENVIRONMENTAL PURPOSES USING A pCO₂ PROBE

[76] Inventor: Jacob D. Paz, 33 Riverside Dr., New York, N.Y. 10023

[21] Appl. No.: 73,432

[22] Filed: Sep. 7, 1979

Related U.S. Application Data

[63] Continuation-in-part of Ser. No. 20,032, Mar. 13, 1979, abandoned.

[51] Int. Cl.³ .......................... C02F 5/06; C02F 3/02; C02F 1/52
[52] U.S. Cl. ................................ 210/614; 210/709; 210/739; 210/754; 210/903; 210/906; 137/5; 204/195 P
[58] Field of Search ................ 210/2, 16, 18, 51, 52, 210/53, 54, 57, 58, 59, 96 R, 42 R, 60, 62, 169, 170; 204/195 P; 137/5, 93; 422/75; 23/230 R

[56] References Cited

U.S. PATENT DOCUMENTS

| | | | |
|---|---|---|---|
| 2,661,332 | 12/1953 | Mortonson | 210/2 |
| 3,129,717 | 4/1964 | Main | 137/93 |
| 3,147,081 | 9/1964 | Stevenson et al. | 204/195 P |
| 3,238,128 | 3/1966 | Gustafson | 137/5 |
| 3,300,404 | 1/1967 | Howe et al. | 210/16 |
| 3,361,150 | 1/1968 | Horner | 137/93 |
| 3,398,079 | 8/1968 | Aruther | 204/195 P |
| 3,592,212 | 7/1971 | Schleimer | 137/93 |
| 3,673,069 | 6/1972 | Niedrach et al. | 204/195 P |
| 3,705,088 | 12/1972 | Niedrach | 204/195 P |
| 3,709,812 | 1/1973 | Niedrach | 204/195 P |
| 3,719,576 | 3/1973 | Macur | 204/195 P |
| 3,844,303 | 10/1974 | Moon | 137/5 |
| 3,957,613 | 5/1976 | Macur | 204/195 P |
| 4,116,834 | 9/1978 | King | 210/63 R |

FOREIGN PATENT DOCUMENTS

2,452,863  5/1975  Fed. Rep. of Germany ........ 210/96 R

OTHER PUBLICATIONS

Betz Handbook of Industrial Water Conditioning 1976, Betz Laboratory, Pa., pp. 51, 52, 25–27, 241, 94, 95, 180, 186.
Clark, Water Supply and Pollution Control, Dun–Donnelley N.Y, 1977 pp. 415, 418.
Limnology, Wetzel, 1975, pp. 167–185.
Water Supply and Pollution Control, Hammer 1977, pp. 431–444, 727, 743, 757.
P.L.T. Floating Covers, 1953, Bulletin No. 332 pp. 15–21.
Standard Methods, Apha, 14th Ed. 1976, pp. 278–282.
Standard Methods, Apha, 14th Ed. 196, 298–300.
1979 Sales Catalog of Joan Cook, 3200 S.E. 14 Avenue, Fort Lauderdale, Fla., p. 85.
Vogel, Textbook of Quantitative Inorganic Analysis, Long man's publication, 1962, 70–71.
"Instruction Manual" for Carbon Dioxide Electrode Model 95-02 published by Orion Research.

*Primary Examiner*—Ernest G. Therkorn
*Attorney, Agent, or Firm*—Lowe, King, Price & Becker

[57] ABSTRACT

A novel method for continuously monitoring and controlling the total alkalinity attributable to carbon dioxide, bicarbonate ion and carbonate ion such as is found in water and waste water treatment systems and in cooling towers. This method includes the steps of sampling the aqueous solution, adjusting the pH of the sample, detecting with a pCO₂ probe the total carbon dioxide of the sample, and adding an alkalinity-controlling chemical to the aqueous solution. Also provided is a method for continuously monitoring this total alkalinity in a natural body of water.

16 Claims, 2 Drawing Figures

METHOD FOR CONTINUOUSLY MONITORING AND CONTROLLING ALKALINITY FOR ENVIRONMENTAL PURPOSES USING A pCO₂ PROBE

REFERENCE TO RELATED APPLICATIONS

This application is a continuation-in-part of co-pending application Ser. No. 020,032, filed Mar. 13, 1979, now abandoned.

TECHNICAL FIELD

This invention relates to a method for continuously monitoring and controlling alkalinity in water and waste water treatment systems and in a cooling tower, and to a method for monitoring alkalinity in a natural body of water.

BACKGROUND ART

Conventionally, alkalinity is monitored by titrating an aqueous sample in the laboratory with a standardized sulfuric acid solution, as described in *Standard Methods*, APHA, 14th Ed., pages 278–282 (1976), and free carbon dioxide is monitored by titrating an aqueous sample with a standardized alkali solution such as sodium carbonate or sodium hydroxide, as described in *Standard Methods*, pages 298–300. Chemicals are then added to the aqueous solution from which the sample is taken, for various purposes such as to adjust alkalinity, cause coagulation of undesired contaminants or to reduce the hardness of the water.

In a biological system such as a water and waste water treatment system, the most meaningful alkalinity value is a measurement of the total alkalinity attributable to carbon dioxide, bicarbonate ion and carbonate ion. One difficulty with the conventional alkalinity titration method is that the alkalinity value determined represents the bicarbonates, carbonates and hydroxides present in the sample.

It is known to sample ground water, sea water, carbonated beverages and wine, and to measure the $pCO_2$ of the sample using a $pCO_2$ probe. This type of prior art is illustrated by the "Instruction Manual" for carbon dioxide electrode model 95-02 published by Orion Research. In this Manual, the user is instructed to adjust the pH of the sample to 4.8 to 5.2 prior to using the $pCO_2$ probe. A substantial problem with such a procedure is that total $pCO_2$ is not measurable at the required pH since a minor amount of carbon dioxide is still present as bicarbonate ion. In addition to this problem, this type of prior art has other deficiencies. It fails to minimize the loss of carbon dioxide to the atmosphere since the procedure is carried out in a system that is open to the atmosphere. Thus, loss of $CO_2$ occurs in handling the sample and in analysis. Also, this type of prior art fails to actively adjust the sample temperature to a selected temperature and then maintain the sample at the selected temperature. Rather, this art only provides for passive temperature equilibration of the sample. Furthermore, this type of prior art does not provide for automatic pH adjustment of the sample but rather provides for a manual adjustment. Moreover, this type of prior art merely measures $pCO_2$ and does not use the result obtained from the measurement to control the total alkalinity.

Other art using carbon dioxide sensors is exemplified by U.S. Pat. Nos. 3,147,081, 3,398,079, 3,673,069, 3,705,088, 3,709,812, 3,719,576 and 3,957,613. This art also uses these sensors only for monitoring purposes, with the primary use being in analyzing small liquid samples such as blood. The probe of U.S. Pat. No. 3,957,613 is capable of simultaneously sensing ion concentrations and partial pressures of gases in a sample, and has been suggested for use in environmental control, sewage being an example.

The use of a pH probe or of a probe capable of sensing dissolved oxygen, ammonia or sulfur dioxide, for only monitoring purposes, has been considered in cooling tower water systems. See Betz *Handbook of Industrial Water Conditioning*, 7th Ed., page 241 (1976).

Finally, it is known to use a pH sensor in an apparatus for increasing the pH of waste water. This type of sensor is deficient in that it cannot measure the total alkalinity attributable to carbon dioxide, bicarbonate ion and carbonate ion. Exemplary of this type of prior art is U.S. Pat. No. 4,116,834 to King.

This and the other prior art of which I am aware is deficient as failing to provide a method for continuously monitoring and controlling the total alkalinity attributable to carbon dioxide, bicarbonate ion and carbonate ion, in an aqueous solution in which it is desirable to maintain alkalinity within a closely controlled range for environmental purposes, and is deficient as failing to provide a method for continuously monitoring the total alkalinity attributable to carbon dioxide, bicarbonate ion and carbonate ion of a natural body of water for environmental purposes.

DISCLOSURE OF THE INVENTION

It is accordingly one object of the present invention to provide a method for continuously monitoring and controlling the total alkalinity attributable to carbon dioxide, bicarbonate ion and carbonate ion in an aqueous solution in which it is desirable to maintain alkalinity within a closely controlled range for environmental purposes.

A further object of the present invention is to provide a method for continuously monitoring the total alkalinity attributable to carbon dioxide, bicarbonate ion and carbonate ion of a natural body of water for environmental purposes.

Other objects and advantages of the present invention will become apparent as the description thereof proceeds.

In satisfaction of the foregoing objects and advantages, there is provided by this invention in a first embodiment, a method for continuously monitoring and controlling the total alkalinity attributable to carbon dioxide, bicarbonate ion and carbonate ion in an aqueous solution. This method includes the steps of sampling the aqueous solution; in a closed system, adjusting the pH of the sample to a value ranging from about 3:1 to 4.5; in a closed system, detecting with a $pCO_2$ probe the total carbon dioxide of the pH-adjusted sample, the sample having been adjusted to and being maintained at a selected temperature value; and adding a sufficient amount of an alkalinity-controlling chemical to the solution to maintain alkalinity within a closely controlled range. This method is useful for any aqueous solution in which it is desirable to maintain alkalinity within a closely controlled range for environmental purposes. Also provided by this present invention in a second embodiment, is a method for continuously monitoring the total alkalinity attributable to carbon dioxide, bicarbonate ion and carbonate ion in a natural body of water. This method includes the steps of sampling the body of water; in a closed system, adjusting the pH of the sample to a value ranging from about 3.1 to 4.5; and in a closed system, detecting with a $pCO_2$ probe the total carbon dioxide of the pH-adjusted sample, the sample having been adjusted to and being maintained at a selected temperature value. This method is useful for determining the total inorganic carbon change in lakes.

BRIEF DESCRIPTION OF THE DRAWING

Reference is hereby made to the accompanying drawing which forms a part of the specification of the present invention.

BEST MODE FOR CARRYING OUT THE INVENTION

Figure 1:
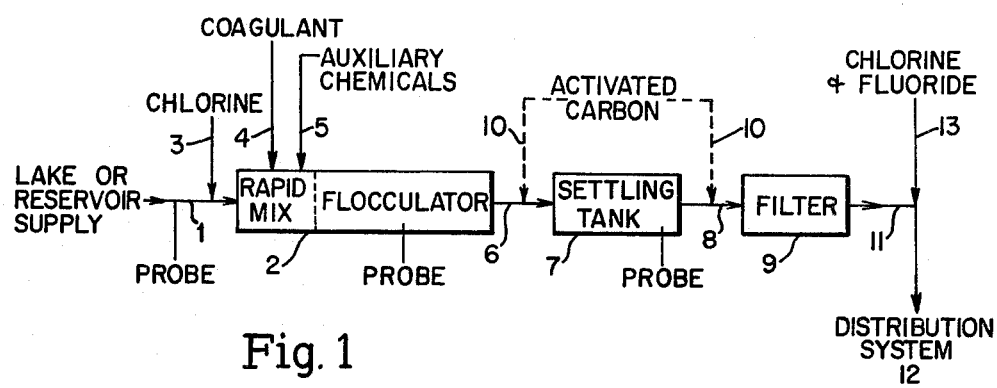
FIG. 1 shows a typical surface-water treatment system for making water provided from a lake or reservoir potable.

As indicated above, the present invention in a first embodiment is concerned with a novel method for continuously monitoring and controlling the total alkalinity attributable to carbon dioxide, bicarbonate ion and carbonate ion in an aqueous solution. According to this novel method, total alkalinity is monitored by first sampling the aqueous solution. The sampling step is suitably accomplished by placing a tube into the aqueous solution and pumping a sample through this tube into a mixing chamber that is closed to the atmosphere. By continuous monitoring and controlling, it is meant that as frequently as about every one or two minutes, a sample is drawn from the aqueous solution and pumped into the mixing chamber. The sampling could be carried out at longer intervals such as about every three or five minutes, but this is not preferable.

In the mixing chamber, the pH of the sample is adjusted to a value ranging from about 3.1 to 4.5, with a value of about 3.5 being preferable except in an anaerobic sludge digestion system, in which a pH value of about 4.5 is preferred. Adjustment of the pH of the sample to within this range is critical to this invention since it results in the conversion of all bicarbonate ion and carbonate ion alkalinity to carbon dioxide alkalinity. At a pH of from 4.8 to 5.2, an error up to 10% will occur due to some bicarbonate ion not having been converted to $CO_2$. Accordingly, adjustment of pH to from about 3.1 to 4.5 is necessary in order to monitor and control total alkalinity attributable to carbon dioxide, bicarbonate ion and carbonate ion.

pH adjustment of the sample is by the addition of an acid such as dilute hydrochloric or sulfuric acid, with a normality of the acid being selected that will produce the required pH adjustment with the addition of a fairly minimum quantity of fluid.

It is preferred that the pH be adjusted automatically rather than manually in order to make possible a rapid measurement of the $pCO_2$ of the sample. A suitable automatic measuring system uses a pH probe to determine the pH of the sample in the mixing chamber. The signal generated by the measured pH value is passed via an amplifier to a comparator which compares the measured pH against a reference pH. The resultant signal from the comparator is passed via an amplifier to a solenoid which adds the required amount of acid to the sample.

The sample is then pumped from the mixing chamber to a measuring chamber that is also closed to the atmosphere. A $pCO_2$ probe is located in the measuring chamber to monitor the $pCO_2$ of the sample. Prior to measuring the $pCO_2$ of the sample, the sample temperature is adjusted to and maintained at a selected temperature value, with a value from in excess of the freezing point to about 40° C. being suitable. A preferred temperature is in the lower portion of this temperature range since carbon dioxide escape to the atmosphere is minimized at lower temperatures. The temperature is suitably adjusted and maintained by locating the mixing chamber and measuring chamber in baths maintained at the selected temperature.

Exemplary probes that may be used for this purpose are disclosed in U.S. Pat. Nos. 3,673,069, 3,705,088, 3,709,812 and 3,719,576 and in the "Instruction Manual" published by Orion Research that is referred to above. There is hereby incorporated by reference into this application the portions of these patents relating to the carbon dioxide sensing probes thereof and the Orion Research "Instruction Manual." These probes are covered by a membrane selective only to $CO_2$. The membrane is in contact with $NaHCO_3$ solution 0.2–0.001 N and 0.9 sodium chloride solution. $TCO_2$ of the acidified solution is diffused through the membrane and rapidly enters $CO_2$ equilibrium with bicarbonate solution alerting its pH, or H+ ion activity.

$$CO_2 + H_2O \rightleftharpoons H_2CO_3 \rightleftharpoons HCO_3^- + H^+$$

The pH of bicarbonate solution is simply a function of $pCO_2$ obtained by rearrangement of the Henderson-Hasselbalch equation.

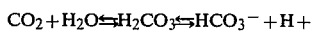

where s is the electrode sensitivity, normally = 0.095–1.00;

where $\alpha$ is the solubility coefficient of $CO_2$ in $HCO_3^-$ solution; and where $Ka_1$ is the first dissociation constant of carbonic acid.

Results are reported as total $CO_2$ mm/Hg and converted into mmoles/l.

Where $pCO_2$ mm/Hg × 0.0301 = mmoles/l $H_2CO_3$, the $HCO_3^-$ concentration mmoles/l can be calculated from the Henderson-Hasselbalch equation:

$$pH = pKa_1 + \log \frac{[HCO_3^-]}{[0.0301 \times pCO_2]},$$

$CO_3^{--}$ ion concentration calculated from: total $CO_2$ alkalinity minus $CO_3^{--} = \Sigma CO_2 - (HCO_3^- + H_2CO_3)$, where $TCO_2$ alkalinity = $H_2CO_3 + HCO_3^- + CO_3^{--}$.

The relationship between alkalinity, pH and $CO_2$ is well known and in this regard there is hereby incorporated by reference into this application pages 415–418 of J. W. Clark. W. Viessman, M. J. Hammer, "*Water Supply and Pollution Control,*" 3rd Ed. (1977).

The $pCO_2$ value determined by the above steps is then used to maintain the alkalinity of the aqueous solution within a closely controlled range by adding a sufficient amount of alkalinity-controlling chemical to the aqueous solution. In a water treatment system, alkalinity is maintained near a value customary for potable water, and in a cooling tower, alkalinity is maintained near a value that will prevent scaling and corrosion of the cooling tower. Alkalinity-controlling chemicals are well known, with an exemplary chemical being lime. The amount of chemical to be added depends upon the chemical selected, the volume of the solution to be treated by the chemical, and the deviation of the value detected by the $pCO_2$ probe from the desired value of the aqueous solution.

As stated above, this embodiment is useful for any aqueous solution in which it is desirable to keep alkalinity within a closely controlled range for environmental purposes. Suitably, the aqueous solution is in a water treatment system or is in a cooling tower. The water treatment system is, for example, a surface water treatment system, a lime-soda ash water softening system, or a waste-water treatment system. The cooling tower is illustratively part of a power plant or heating system.

Referring to FIG. 1, there is shown a typical surface-water treatment system for rendering water drawn from a lake or reservoir potable. In this Figure, water is fed from the lake or reservoir by line 1 to rapid mix-flocculator 2. Prior to entry of the water into rapid mix-flocculator 2, chlorine is added thereto by line 3. In the rapid mixing zone of rapid mix-flocculator 2, coagulant and auxiliary chemicals are added to the water by lines 4 and 5, respectively. The auxiliary chemicals include alkalinity-controlling chemicals. The water is passed by line 6 from rapid mix-flocculator 2 to settling tank 7, and overflow from settling tank 7 is passed by line 8 to filter 9. Activated carbon is added to line 6 or line 8 by line 10, if necessary. The filtered water is passed by line 11 from filter 9 to distribution system 12. Chlorine and fluoride are added by line 13 to the water in line 11. In this system, the water is sampled at the points indicated by the word "probe." These points are the indicated point in line 1, in rapid mix-flocculator 2 and in settling tank 7. The point in line 1 is before any treatment step. In rapid mix-flocculator 2 the water is suitably sampled near the point of outflow from this tank, and in settling tank 7 the water is suitably sampled near the point of outflow from the tank.

A typical surface-water treatment system for preparing water drawn from a river supply for use as drinking water is similar to the system shown in FIG. 1. However, two differences are use of a presedimentation basin prior to feeding the water to a rapid mix-flocculator, and use of an additional rapid mix-flocculator apparatus and an additional settling tank. The water is sampled in this type of system at the three points described above, with there being a sample taken from each of the flocculators and each of the settling tanks.

Figure 2:
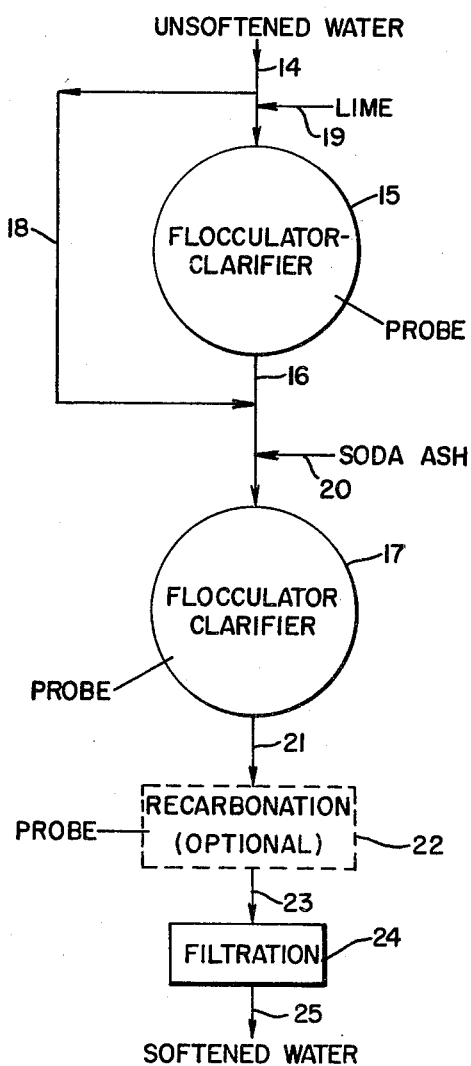
FIG. 2 depicts a typical split treatment lime-soda ash water softening system.

The method of the present invention is also useful in a lime-soda ash water softening system, the chemistry of which is well known. In this regard, there is hereby incorporated by reference into this application pages 431–444 of *Water Supply and Pollution Control*. There are three basic types of this system: excess lime treatment, selective calcium removal and split treatment. Referring to FIG. 2, there is shown, for illustrative purposes, a split-treatment softening system. In this Figure, part of a solution of unsoftened water is fed by line 14 to flocculator-clarifier 15 and then passed by line 16 to flocculator-clarifier 17, and the other part of the solution is fed by bypass line 18 to line 16 where it recombines with the treated part of the solution. Lime is added by line 19 to the part of the solution being fed by line 14 to flocculator-clarifier 15, the soda ash is added by line 20 to the combined treated and untreated solutions in line 16. The solution from flocculator-clarifier 17 is optionally fed by line 21 to recarbonation tank 22, and the outflow from tank 22 is fed by line 23 to filtration area 24, from which softened water is passed by line 25. With reference to FIG. 2, water is sampled at the points indicated by the word "probe." These points are in line 14 at a point prior to lime being added by line 19, in flocculator-clarifier 15, in flocculator-clarifier 17, and in recarbonation tank 22. If it is not necessary to feed the solution to tank 22, then the present invention requires only a sample from line 14 and from flocculator-clarifiers 15 and 17.

A typical excess lime treatment system for softening water is set forth in FIG. 10-8 at page 434 of *Water Supply and Pollution Control*. In this system, unsoftened water is fed to a flocculator-clarifier, then to a recarbonation tank, then to another flocculator-clarifier, then to another recarbonation tank and finally to a filtration area. Lime and soda ash are added to the unsoftened water before the water enters the first flocculator-clarifier. In this system, a sample is taken from the inflow line to the first flocculator-clarifier at a point prior to any chemical treatment of the unsoftened water, from each of the flocculator-clarifiers, and from each of the recarbonation tanks.

The method of the present invention is also useful in waste water treatment systems. Exemplary systems of this type are for the removal of phosphorus, biological nitrification, breakpoint chlorination and anaerobic sludge digestion.

Waste water treatment systems for the removal of phosphorus, use chemical precipitation with activated-sludge treatment, precipitation by use of lime or tertiary treatment by chemical precipitation. Schemes for these types of phosphorus removal are set forth in FIG. 13-10 at page 727 of *Water Supply and Pollution Control*. This Figure and the accompanying descriptive material are hereby incorporated by reference into this application. In the scheme for phosphorus precipitation by use of lime, a sample is taken from the aqueous solution at a point prior to the addition of the lime. In the tertiary treatment by chemical precipitation scheme, treated waste water from biological secondary treatment is fed into a rapid mixing tank where chemicals including alkalinity-controlling chemicals are added, then to a flocculator tank, then to a sedimentation tank, and finally to a filtration area. In this system, a sample is taken from the treated waste water prior to entry into the rapid mixing tank, and from the sedimentation tank.

A typical system for biological nitrification is set forth in FIGS. 13-19 at page 743 of *Water Supply and Pollution Control*. This Figure and the pertinent descriptive material relating thereto are hereby incorporated by reference into this application. In this system, waste water that has been processed by conventional biological treatment is passed into a compartmented aeration tank and then into a sedimentation tank. An alkali such as sodium bicarbonate or lime is added, as necessary, for alkalinity and pH control to each of the compartments in the aeration tank. A diffused or mechanical aeration is used in the aeration tank. In this system, the processed waste water is sampled at a point prior to entry into the aeration tank, and the water in each of the compartments of the compartmented tank is sampled.

A typical system for breakpoint chlorination is set forth in FIGS. 13-28 at page 757 of *Water Supply and Pollution Control*. This Figure and the pertinent discussion relating thereto are hereby incorporated by reference into this application. In this system, the water is sampled at a point prior to any treatment by the system and is sampled in the breakpoint chamber of the system.

A typical anaerobic sludge digestion system uses a single stage floating cover digester. This type of digester is illustrated in FIGS. 11-48 at page 420 of M. J. Hammer, *Water and Waste Water Technology* (1975). This Figure and the descriptive material pertinent to it are hereby incorporated by reference into this application. In this system, gases from the outflow gas pipe are flowed into an aqueous trap and a sample is taken from the trap. A sample is also taken from the pipe for drawing off supernatant. These samples are preferably adjusted to a pH value of about 4.5 prior to monitoring $pCO_2$.

In addition to the water treatment systems discussed above, this embodiment is useful for continuously monitoring and controlling the total alkalinity attributable to carbon dioxide, bicarbonate ion and carbonate ion, of well water and of an aqueous solution in a cooling tower such as is part of a power plant or heating system. In a cooling tower, alkalinity is maintained at a value to prevent scaling or corrosion by known procedures which include adding an alkalinity-controlling chemical. The problem of scaling and corrosion, and the relationship of alkalinity to this problem is discussed in Betz, *Handbook of Industrial Water Conditioning*, 7th Ed. pages 94, 95, 180 and 186 (1976). This disclosure is hereby incorporated by reference into this application.

The systems discussed for this embodiment are merely typical and illustrative, and therefore the scope of the invention is in no way to be limited to them.

In a second embodiment of this invention, there is provided a method for continuously monitoring the total alkalinity attributable to carbon dioxide, bicarbonate ion and carbonate ion, of a natural body of water such as a lake. During thermal stratification of a lake, changes occur in the vertical distribution of carbon dioxide and in the total inorganic carbon. In this regard, there is hereby incorporated by reference into this application pages 167–185 of R. G. Wetzel, *Limnology* (1975). By sampling different depths of the lake, changes in the vertical distribution of carbon dioxide with thermal stratification and in the total inorganic carbon are monitored. This embodiment corresponds in all details to the first embodiment described except that only monitoring is involved.

I claim:

1. A method for continuously monitoring and controlling the total alkalinity attributable to carbon dioxide, bicarbonate ion and carbonate ion in an aqueous solution in which it is desirable to maintain alkalinity near a value customary for drinking water for environmental purposes, said method comprising the steps of
   (a) sampling the aqueous solution,
   (b) in a closed system automatically adjusting the pH of the sample to a value of about 3.5,
   (c) in a closed system detecting with a $pCO_2$ probe the total carbon dioxide of the pH-adjusted sample, the sample having been adjusted to and being maintained at a selected temperature value, and
   (d) adding a sufficient amount of an alkalinity-controlling chemical to said solution to maintain alkalinity near a value customary for drinking water.

2. The method of claim 1 wherein the aqueous solution is in a water treatment system.

3. The method of claim 2 wherein the water treatment system is a surface-water treatment system.

4. The method of claim 3 wherein said surface-water treatment system comprises a flocculator and a settling tank; wherein the aqueous solution is sampled at a point prior to any treatment step being carried out in said system; wherein the aqueous solution is sampled in the flocculator; and wherein the aqueous solution is sampled in the settling tank.

5. The method of claim 2 wherein the water treatment system is a lime-soda ash water softening system.

6. The method of claim 5 wherein said softening system comprises a flocculator-clarifier; wherein the aqueous solution is sampled at a point prior to any treatment step being carried out in said system; and wherein the aqueous solution is sampled in the flocculator-clarifier.

7. The method of claim 6 wherein said softening system further comprises a recarbonation tank, and wherein the aqueous solution is additionally sampled in said tank.

8. The method of claim 2 wherein the water treatment system is a waste water treatment system.

9. The method of claim 8 wherein said waste water treatment system is a phosphorus removal system.

10. The method of claim 9 wherein said phosphorus removal system uses lime as the precipitating agent for the removal of phosphorus, and wherein the aqueous solution is sampled at a point prior to the lime being added to said solution.

11. The method of claim 9 wherein said phosphorus removal system uses tertiary treatment by chemical precipitation for phosphorus removal; wherein said phosphorus removal system comprises a sedimentation tank; wherein the aqueous solution is sampled at a point prior to the addition of the additives for chemical precipitation; and wherein the aqueous solution is sampled in the sedimentation tank.

12. The method of claim 8 wherein said waste water treatment system is a biological nitrification system.

13. The method of claim 12 wherein said nitrification system comprises a compartmented aeration tank; wherein the aqueous solution is sampled at a point prior to any treatment step being carried out in said nitrification system; and wherein the aqueous solution is sampled in each compartment of said aeration tank.

14. The method of claim 8 wherein said waste water treatment system is a breakpoint chlorination system.

15. The method of claim 14 wherein said chlorination system comprises a breakpoint chamber; wherein the aqueous solution is sampled at a point prior to any treatment step being carried out in said chlorination system; and wherein the aqueous solution is sampled in said breakpoint chamber.

16. The method of claim 1 wherein the aqueous solution is in a cooling tower.

* * * * *